United States Patent
Kim et al.

(10) Patent No.: US 12,310,995 B2
(45) Date of Patent: May 27, 2025

(54) GUT MICROBES AGAINST INFECTIOUS DISEASES AND ITS USE

(71) Applicants: SNJ PHARMA INC, Torrance, CA (US); Hyeon Jin Kim, Torrance, CA (US)

(72) Inventors: Hyeon Jin Kim, Torrance, CA (US); Seong Tshool Hong, Jeonju-si (KR); Jinny Hong, Torrance, CA (US); Mingda Wang, Jeonju-si (KR); Enkhchimeg Lkhagva, Jeonju-si (KR); Su Ra Kim, Jeonju-si (KR); Hae Mi Kim, Jeonju-si (KR)

(73) Assignees: SNJ PHARMA INC., Torrance, CA (US); Hyeon Jin Kim, Torrance, CA (US)

( * ) Notice: Subject to any disclaimer, the term of this patent is extended or adjusted under 35 U.S.C. 154(b) by 0 days.

(21) Appl. No.: 18/409,857

(22) Filed: Jan. 11, 2024

(65) Prior Publication Data
US 2024/0238351 A1   Jul. 18, 2024

(30) Foreign Application Priority Data
Jan. 12, 2023 (KR) .................. 10-2023-0004607

(51) Int. Cl.
| | | |
|---|---|---|
| A61K 39/02 | (2006.01) | |
| A61K 35/74 | (2015.01) | |
| A61P 31/06 | (2006.01) | |
| A61P 31/16 | (2006.01) | |
| C12N 1/20 | (2006.01) | |

(52) U.S. Cl.
CPC ............ *A61K 35/74* (2013.01); *A61P 31/06* (2018.01); *A61P 31/16* (2018.01); *C12N 1/20* (2013.01)

(58) Field of Classification Search
CPC ....... A61K 35/74; A61K 35/741; A61P 31/06; A61P 31/00; C12N 1/20; C12N 1/205; C12R 2001/01
See application file for complete search history.

(56) References Cited

U.S. PATENT DOCUMENTS

| | | |
|---|---|---|
| 10,195,273 B2 | 2/2019 | Clube |
| 11,471,495 B2 | 10/2022 | Pamer et al. |
| 2020/0009168 A1 | 1/2020 | von Maltzahn et al. |
| 2020/0376044 A1 | 12/2020 | Han et al. |
| 2021/0332323 A1 | 10/2021 | Kim et al. |
| 2022/0347229 A1 | 11/2022 | Yoon et al. |

FOREIGN PATENT DOCUMENTS

| | | |
|---|---|---|
| EP | 2797606 A2 | 11/2014 |
| EP | 3559209 A1 | 10/2019 |
| EP | 3661525 A1 | 6/2020 |
| JP | 2014528925 A | 10/2014 |
| JP | 2020529478 A | 10/2020 |
| WO | 2013032744 A2 | 7/2013 |
| WO | 2016086161 A1 | 6/2016 |
| WO | 2016172658 A2 | 10/2016 |
| WO | 2018117263 A1 | 6/2018 |
| WO | 2019028402 A1 | 2/2019 |
| WO | 2021066585 A1 | 4/2021 |
| WO | 2021194281 A1 | 9/2021 |

OTHER PUBLICATIONS

Hirayama Masaaki et al: "Intestinal Collinsella may mitigate infection and exacerbation of COVID-19 by producing ursodeoxycholate", PLOS One, vol. 16, No. 11, Nov. 23, 2021 (Nov. 23, 2021), p. e0260451, XP093070654, DOI: 10.1371/journal.pone. 0260451.

Julia A. Brown: "Gut microbiota-derived metabolites confer protection against SARS-CoV-2 infection", Gut Microbes, vol. 14, No. 1, Aug. 1, 2022 (Aug. 1, 2022), XP093152470, United States ISSN: 1949-0976, DOI: 10.1080/19490976.2022.2105609.

*Primary Examiner* — Jennifer E Graser
(74) *Attorney, Agent, or Firm* — NKL Law; Jae Youn Kim

(57) ABSTRACT

Gut microbes to provide a preventive or therapeutic effect on infectious diseases caused by pathogenic microorganisms and uses thereof are discussed. The gut microbes resistant are characterized in that they are selected from the group consisting of *Oribacterium* species JBO3-101 (accession number KACC 81250BP) and *Ruminococcus* species JBR5-501 (accession number KACC 81249BP). The gut microbes according to the present disclosure have the effect of rendering the host resistant to infectious diseases caused by pathogenic microorganisms when the microbes are ingested.

6 Claims, 18 Drawing Sheets
Specification includes a Sequence Listing.

SEQUENCE LISTING

```
Sequence total quantity: 4
SEQ ID NO: 1            moltype = DNA  length = 20
FEATURE                 Location/Qualifiers
source                  1..20
                        mol_type = other DNA
                        organism = synthetic construct
```

```
SEQUENCE: 1
agagtttgat cctggctcag                                                    20

SEQ ID NO: 2           moltype = DNA   length = 19
FEATURE                Location/Qualifiers
source                 1..19
                       mol_type = other DNA
                       organism = synthetic construct
SEQUENCE: 2
ggttaccttg ttacgactt                                                     19

SEQ ID NO: 3           moltype = DNA   length = 1408
FEATURE                Location/Qualifiers
source                 1..1408
                       mol_type = other DNA
                       organism = Oribacterium sp.
SEQUENCE: 3
tgcaagtcga acgagatgcg ttattggaaa gcttcggccg gaagatgcgt tatctagtgg         60
cggacgggtg agtaacacgt gggtaacctg ccttatggag ggggataaca gagagaaatc        120
actgctaata ccgcataagc acacagtacc gcatggcaga gtgtgaaaag atttatcgcc        180
ataagatgga cccgcgtctg attagccagt tggcagggta aaagcctacc aaagcaacga        240
tcagtagccg atctgagagg atgaccggcc acattgggac tgagacacga cccaaactcc        300
tacgggaggc agcagtgggg aatattgcac aatgggggaa accctgatgc agcgaacgcc        360
gcgtgagtga agaagtattt cggtatgtaa agctctatca gcagggaaga taatgacagt        420
acctgactaa gaagccccgg ctaactacgt gccagcagcc gcggtaatac gtaggggca         480
agcgttatcc ggatttactg ggtgtaaagg gagcgtagac ggagtggcaa gtctgaagtg        540
aaaaccctgg gcttaacctg gggactgctt tggaaactgt taatctagag tgttggagag        600
gtaagtggaa ttcctggtgt agcggtgaaa tgcgtagata tcaggaagaa caccggaggc        660
gaaggcggct tactggacaa taactgacgt tgaggctcga aagcgtgggg atcaaacagg        720
attagatacc ctggtagtcc acgctgtaaa cgatgaatac taggtgtcgg gggagcaaag        780
cttctcggtg ccgtcgctaa cgcaataagt attccacctg gggagtacgt tcgcaagaat        840
gaaactcaaa ggaattgacg gggacccgca caagcggtgg agcatgtggt ttaattcgaa        900
gcaacgcgaa gaaccttacc aagtcttgag atcccattga cagagtgtgt aatgcatttt        960
cccttcgggg caatgggtga caggtggtgc atggttgtcg tcagctcgtg tcgtgagatg       1020
ttgggattaa gttcccgcaa cgagcgcaac ccctatagtt agtagtccag cagtaagatg       1080
ggacactcta actagactgc cagggataac ctggaggaag gcgggatga cgtcaaatca        1140
tcatgcccct tatgacttgg gctacacacg tgctacaatg gcgtaaacaa agggaagcaa       1200
gagggtgacc ttaagcaaat ctcaaaaata acgtctcagt tcggactgta gtctgcaacc       1260
cgactacacg aagctggaat cgctagtaat cgcagatcag catgctgcgg tgaatacgtt       1320
cccgggtctt gtacacaccg cccgtcacac catgggagtt ggtaatgccc gaagtcagtg       1380
tcccaagaga gggagctgcc gaaggcag                                          1408

SEQ ID NO: 4           moltype = DNA   length = 1417
FEATURE                Location/Qualifiers
source                 1..1417
                       mol_type = other DNA
                       organism = Ruminococcus gnavus
SEQUENCE: 4
ccttcggcag ctccctcctt gcggttgggt cactgacttc gggcgttact gactcccatg         60
gtgtgacggg cggtgtgtac aagacccggg aacgtattca ccgcgacatt ctgattcgcg        120
attactagcg attccagctt catgtagtcg agttgcagac tacaatccga actgagacgt        180
tattttggg atttgctccc cctcgcgggc tcgcttccct ttgtttacgc cattgtagca        240
cgtgtgtagc cctggtcata aggggcatga tgatttgacg tcatcccac cttcctccag         300
gttatccctg gcagtctctc tagagtgccc atccaaaatg ctggctacta aagataggg         360
ttgcgctcgt tgcgggactt aacccaacat ctcacgacac gagctgacga caaccatgca        420
ccacctgtct cctctgtccc gaaggaaagc tccgattaaa gagcggtcag agggatgtca        480
agaccaggta aggttcttcg cgttgcttcg aattaaacca catgctccac cgcttgtgcg        540
ggtccccgtc aattcctttg agtttcattc ttgcgaacgt actccccagg tggaatactt        600
attgcgtttg ctgcggacac gaatggcttt gccaccgac acctagtatt catcgtttac        660
ggcgtggact accagggtat ctaatcctgt ttgctcccca cgctttcgag ccctcaacgt        720
cagtcatcgt ccagaaagcc gccttcgcca ctggtgttcc tcctaatatc tacgcatttc        780
accgctacac taggaattcc gctttcctct ccgacactct agcctgacag ttccaaatgc        840
agtcccgggg ttgagcccg gcttttcaca tctggcttgc catgccgtct acgctccctt         900
tacacccagt aaatccggat aacgcttgcc cctacgtat taccgcggct gctggcacgt        960
agttagccgg gcttcttag tcaggtaccg tcattttctt ccctgctgat agagcttac         1020
ataccgaaat acttcatcgc tcacgcgcg tcgctgcatc agggtttccc ccattgtgca        1080
atattcccca ctgctgcctc ccgtaggagt ttgggccgtg tctcagtccc aatgtggccg       1140
gtcaccctct caggtcggct actgatcgtc ggcttggtag gccgttaccc cagccaacta       1200
cctaatcaga cgcgggtcca tctcatacca ccggagtttt tcacaccgta ccatgcggta       1260
ctgtgcgctt atgcggtatt agcagccgtt tccaactgtt atcccctgt atgaggcagg       1320
ttacccacgc gttactcacc cgtccgccgc tcagtcacca aggcttcaat ccgaagaaat       1380
ccgtcaaggt gcttcgctcg acttgcatgg gttaagc                                1417
```

GUT MICROBES AGAINST INFECTIOUS DISEASES AND ITS USE

CROSS REFERENCE TO RELATED APPLICATION

The present application claims priority to Korean Patent Application No. 10-2023-0004607, filed Jan. 12, 2023, the entire contents of which is incorporated herein for all purposes by this reference.

INCORPORATION OF SEQUENCE LISTING

This application contains a sequence listing submitted in Computer Readable Form (CRF). The CRF file containing the sequence listing entitled "PK3806518.xml," which was created on Jan. 10, 2024, and is 7,218 bytes in size. The information in the sequence listing is incorporated herein by reference in its entirety.

BACKGROUND OF THE DISCLOSURE

1. Field of the Disclosure

The present disclosure relates to gut microbes against infectious diseases and uses thereof. More particularly, the present disclosure relates to gut microbes resistant against infectious diseases, which provide a preventive or therapeutic effect on infectious diseases caused by pathogenic microorganisms and to uses thereof.

2. Description of the Related Art

Since the dawn of history, humankind has been in a constant battle with pathogens. With the development of antibiotics, antivirals, and vaccines, the problem of infectious diseases has been largely solved. However, recent changes in climate and environment like global warming, changes in living conditions and human lifestyles, and the evolutionary characteristics of microorganisms have led to the emergence of new and more lethal pathogens. In particular, SARS-CoV-2, which emerged in late 2019 as well as tuberculosis, Ebola, MERS, and SARS are wreaking havoc on the world's population. The severity of COVID-19 has led to the development of a number of preventative vaccines. In addition to traditional vaccines, mRNA vaccines have been developed, and as of December 2022, more than 70% of the human population had received at least one dose of a COVID-19 vaccine. However, South Korea, where 87% of the population had been vaccinated with an mRNA vaccine, had the highest per capita rate of COVID-19 in the world, indicating more than 10 times that of third world countries with vaccination rates ranging from 10%-30%. Therefore, it is urgent to develop a breakthrough vaccine that can prevent infectious diseases regardless of the type or mutation of the pathogen unlike existing vaccines.

The gut microbiota or microbiome has a significant impact on the overall health conditions of the host as well as on diseases such as obesity, diabetes, dementia, cancer, cardiovascular disease, and the like. As a result of active research over the past 20 years, it is now known that the gut microbes colonizing in an environment exposed to a variety of pathogens has influence on the resistance of the host against infectious diseases. For this reason, it is considered that there is a wide range of host resistance levels to the same pathogen: for example, non-infectious, asymptomatic, or severe disease when exposed to the same pathogen.

For the reasons described above, the technologies described below have been developed to develop infection-resistant microbiomes that can prevent or treat infectious diseases caused by pathogenic microorganisms.

U.S. Ser. No. 11/471,495 discloses microbes of *C. scindens, C. hiranonis, C. hylemonae, C. perfringens, C. sordelli, Proteocatella sphenisci*, Lachnospiraceae 5_1_57 FAA, *Barnesiella intestihominis, Blautia hansenii*, and *Pseudoflavonifractor capillosus* as gut microbes for preventing infection with the pathogenic bacterium *Clostridium difficile*.

WO2021066585 and US20220347229 disclosure *Staphylococcus epidermidis* as a gut microbe with an immune-enhancing effect against some pathogenic bacteria.

WO2016086161 discloses *Ruminococcus obeum, C. hathewayi, Eubacterium desmolans, Dorea longicatena, R. lactaris* (*Blautia producta*), *Eubacterium contorum, R. faecis, Holdemania filiformis*, and *C. sordelli* as gut microbes for the treatment of prophylaxis.

U.S. Ser. No. 10/195,273 discloses *Akkermansia* or *Faecalibacterium* as a gut microbe that functions as a PD-1 inhibitor or PD-L1 inhibitor.

WO2019028402, US2020376044, JP32529478, and EP03661525 disclose *Roseburia hominis* and *Eubacterium eligens* for treating metabolic diseases.

WO2018117263 and EP03559209 disclose *Phascolarctobacterium faecium* LN998073, *Fusobacterium ulcerans* KR822463, *Bacteroides dorei* CP011531, *B. uniformis* NR_112945, *Subdoligranulum* sp. 4_3_54 A2FAA, *Paraprevotella xylaniphila* AB331897, *Parabacteroides johnsonii* AB261128, *Alistipes* sp. JC136 NZ-CAEG00000000, *P. gordonii* AB470343, *Eubacterium limosum* AB595134, *P. distasonis* HE974920, *B. cellulosilyticus*_NR_112933, *B. clarus*_AB490801, *B. salyersiae*_AY608696, *B. fragilis*_CR626927, *B. uniformis*_AB247141, *B. eggerthii*_NR_112935.

WO2021194281 discloses *Akkermansia muciniphila* strain or products thereof for the prevention and treatment of inflammatory diseases.

WO2013032744, JP26528925, and EP02797606 disclose a composition that increases the proportion of Firmicutes relative to Bacteroidetes phylum in the gut microbe.

WO2016172658 and US20200009168 disclose sugars, sugar alcohols, amino acids, peptides, micronutrients, fatty acids, or polyphenols as microbe regulator compositions.

US20210332323 discloses *L. plantarum* CJLP475, which has antiviral and immunomodulatory effects by increasing the secretion of cytokines, as a feed additive.

However, the technologies mentioned above lack infection resistance, and there are no successful examples of gut microbes that can prevent or treat serious infectious diseases caused by pathogenic microorganisms. In the case of COVID-19, despite a number of attempts, no gut microbes resistant to SARS-CoV-2 virus have been identified at the species level. Therefore, the development of gut microbes to prevent or treat infectious diseases caused by various pathogenic bacteria and viruses is urgently needed.

The present disclosure relates to gut microbes against infectious diseases and uses thereof. The present disclosure also relates to gut microbes against infectious diseases, the microbes providing preventive or therapeutic effects on infectious diseases caused by pathogenic microorganisms, and to uses thereof.

SUMMARY OF THE DISCLOSURE

An objective of the present disclosure is to provide gut microbes against infectious diseases.

Another objective of the present disclosure is to provide gut microbes against infectious diseases, which provide preventive or therapeutic effects on infectious diseases caused by pathogenic microorganisms, and uses of the gut microbes.

To achieve the above objectives, the present disclosure provides gut microbes against infectious diseases, which provide a preventive or therapeutic effect on an infectious disease caused by a pathogenic microorganism, the gut microbes being selected from the group consisting of *Oribacterium* sp. JBO3-101 strain and *Ruminococcus* sp. JBR5-501 strain. Under the provisions of the Budapest Treaty on the International Recognition of the Deposit of Microorganisms for the Purposes of Patent Procedure, both strains were deposited with the international depositary authority: the Korean Collection for Type Cultures (KACC) of Biological Resource Center in Korea Research Institute of Bioscience & Biotechnology (KRIBB) on Dec. 20, 2022. The JBO3-101 strain was under the accession number KACC 81250BP and the JBR5-501 strain was under the accession number KACC 81249BP.

The present disclosure also provides a preventive or therapeutic composition for infectious diseases, the composition containing, as an active ingredient, one or more gut microbes against infectious diseases, or cultures thereof, selected from the group consisting of *Oribacterium* species JBO3-101 strain (accession number KACC 81250BP) and *Ruminococcus* species JBR5-501 strain (accession number KACC 81249BP).

The present disclosure also provides a method for preventing or treating infectious diseases by administering, to a mammal, one or more gut microbes against infectious diseases, or cultures thereof, selected from the group consisting of *Oribacterium* species JBO3-101 strain (accession number KACC 81250BP) and *Ruminococcus* species JBR5-501 strain (accession number KACC 81249BP).

The gut microbes against infectious diseases according to the present disclosure have the effect of rendering the host resistant to infectious diseases caused by pathogenic microorganisms when ingested.

DESCRIPTION OF THE PREFERRED EMBODIMENTS

Figure 1:
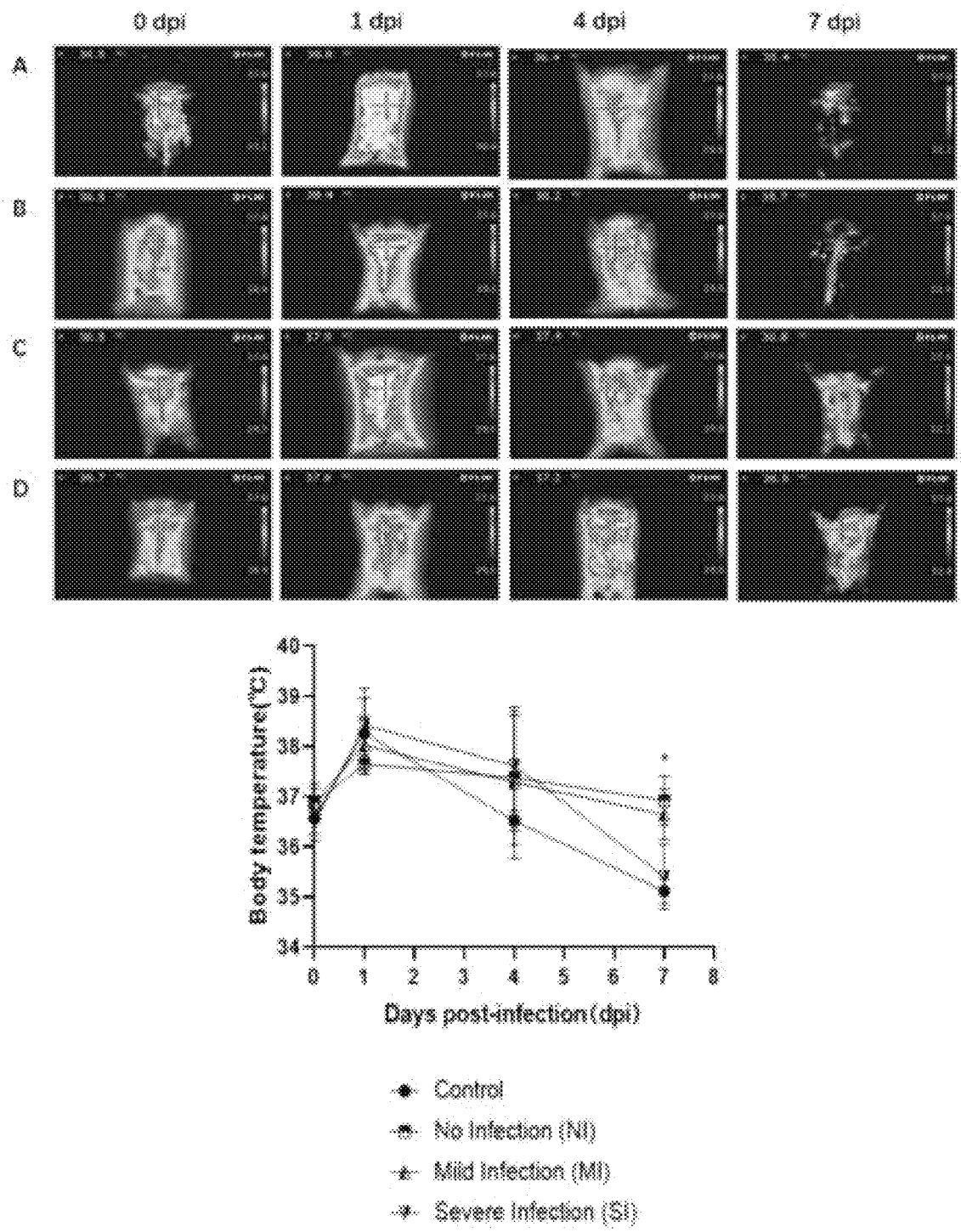
FIG. 1 shows images (top) and graphs (bottom) of body temperature measurements of groups of experimental animals classified by degree of infection with SARS-CoV-2 virus after ingestion of an infection-resistant human gut microbe according to Example 1 of the present disclosure (A: control group, B: severely infected group, C: mildly infected group, D: non-infected group).

The gut microbiota or microbiome has a significant impact on the overall health conditions of the host as well as on diseases such as obesity, diabetes, dementia, cancer, cardiovascular disease, and the like. Gut microbes colonizing in an environment exposed to a variety of pathogens has influence on the resistance of the host against infectious diseases. For this reason, it is considered that there is a wide range of host resistance levels to the same pathogen: for example, non-infectious, asymptomatic, or severe disease when exposed to the same pathogen.

The inventors have made the present disclosure by focusing on the fact that infection-resistant microbes would form colonies in the intestines of people who had not been infected even when exposed to pathogenic microorganisms.

Accordingly, the inventors prepared feces samples from infection-resistant individuals who never contracted COVID-19 even though they were exposed to the virus during the coronavirus pandemic. Next, COVID-19 model experimental animals were treated with an antibiotic/antibacterial complex, then the prepared faces samples were ingested by the animals, and the animals were infected with the SARS-CoV-2 virus. The screening succeeded in identifying infection-resistant animals that showed no symptoms of infection after the SARS-CoV-2 infection, and their gut microbe analysis identified two infection-resistant microbes, JBO3-101 and JBR5-501, which were confirmed to be novel by 16s RNA sequencing.

The inventors have confirmed the protective effect against SARS-CoV-2 virus infection in experimental animals in which a de novo microbiome was created using the BO3-101 and JBR5-501 strains, which were discovered as microbes resistant against infectious diseases.

The inventors also treated experimental animals infected with influenza virus, which is the most common viral infectious disease microorganism, with the gut microbes JBO3-101 and JBR5-501 to confirm the flu treatment effect.

To confirm the preventive effect against *Mycobacterium tuberculosis*, which causes one of the most serious bacterial infectious diseases, the inventors created a de novo microbiome in experimental animals using the microbes JBO3-101 and JBR5-501, which were identified as microbes resistant against infectious, and then confirmed the preventive effect against *Mycobacterium tuberculosis* infection.

In one example of the present disclosure, there is provided a gut microbe against infectious diseases, the microbe providing preventive or therapeutic effect on infectious diseases caused by pathogenic microorganisms, and uses of the gut microbes are also provided.

Accordingly, in one aspect, the present disclosure relates to a gut microbe against infectious diseases, the microbe being selected from the group consisting of *Oribacterium* sp. JBO3-101 strain (accession number KACC 81250BP) and *Ruminococcus* sp. JBR5-501 strain (accession number KACC 81249BP).

Additionally, the present disclosure relates to a preventive or therapeutic composition for infectious diseases, the composition containing, as an active ingredient, one or more gut microbes against infectious diseases or cultures thereof selected from the group consisting of *Oribacterium* sp. JBO3-101 strain (accession number KACC 81250BP) and *Ruminococcus* sp. JBR5-501 strain (accession number KACC 81249BP).

In the present disclosure, the infectious disease refers to a disease caused by infection with a pathogenic virus (viral infection), a pathogenic bacterium (bacterial infection), or a pathogenic fungus (fungal infection).

The viral infection includes any infection caused by a pathogenic virus, and specific examples of the pathogenic viruses include severe acute respiratory syndrome virus (SARS-COV), hepatitis B virus, hepatitis C virus, human papillomavirus, influenza virus, human immunodeficiency virus (HIV), Ebola virus, dengue virus, measles virus, Hantan virus, rubella virus, rotavirus, and norovirus.

The bacterial infection includes any infection caused by a pathogenic bacterium, and specific examples of the pathogenic bacteria include *Mycobacterium tuberculosis*, *Streptococcus pneumoniae*, *Vibrio cholerae*, *Diphtheria bacillus*,

*Mycobacterium leprae, Treponema pallidum, Tetanus bacillus,* and *Sallmonella typhi* but are not limited thereto.

The fungal infection includes any infection caused by a pathogenic fungus, and specific examples of the pathogenic fungi include *Aspergillus* sp., *Candida* sp., Yeast, *Histoplasma* sp., *Coccidioides* sp., and *Sporothrix* sp. but are not limited thereto.

The composition for preventing or treating an infectious disease is not particularly limited, but preferably contains microbes of $10^3$ to $10^{12}$ cfu/g.

In the present disclosure, the culture may be a culture itself obtained by culturing the microbes, or a culture supernatant obtained by removing the microbes therefrom, or a concentrate or lyophilisates of the culture supernatant.

In the present disclosure, the composition for preventing or treating an infectious disease can be administered to a mammal, including a human, via various routes. The way in which the composition is administered may be any conventionally used way. For example, the composition may be administered via an oral, dermal, intravenous, intramuscular, or subcutaneous route, and preferably by oral administration.

The composition may include a pharmaceutically acceptable excipient or carrier. The pharmaceutically acceptable excipients and diluents for therapeutic use are well known in the field of pharmacy. Suitable examples of the carrier include lactose, starch, glucose, methyl cellulose, magnesium stearate, mannitol, sorbitol, etc. Suitable examples of the diluent include ethanol, glycerol, and water. The choice of the pharmaceutical carrier, excipient, or diluent may be made depending on the intended route of administration and standard pharmaceutical practice. The composition may further include any suitable binder, lubricant, suspending agent, coating agent, solubilizer, as or in addition to the carrier, excipient, or diluent.

When the composition is formulated, the formulations or preparations are prepared using commonly used diluents or excipients such as fillers, extenders, binders, wetting agents, disintegrants, and surfactants. Solid formulations for oral administration include tablets, pills, powders, granules, capsules, and the like. These solid formulations are formulated by adding at least one excipient such as starch, calcium carbonate, sucrose, lactose, gelatin, and the like to the composition described above. Aside from the simple excipients, lubricants such as magnesium stearate, talc, or the like may be additionally used.

Liquid formulations for oral administration may include suspensions, solutions, emulsions, and syrups. Aside from a simple diluent such as water or liquid paraffin, the oral formulations may additionally contain various excipients such as wetting agents, sweetening agents, fragrances, preservatives, and the like. Formulations for parenteral administration include sterile aqueous solutions, non-aqueous solutions, suspensions, emulsions, and lyophilized preparations. For the non-aqueous solutions and suspensions, propylene glycol, polyethylene glycol, vegetable oils such as olive oil, injectable esters such as ethylolate, and the like may be used. The components may be used in combination with the active ingredient such as a mixed mycelium, a culture thereof, an extract thereof, or a mycelial component thereof.

The optimal dosage of the pharmaceutical compositions according to the present disclosure may vary depending on factors such as a formulation method, an administration mode, the age, weight, sex, and medical condition, and dietary of the patient, time of administration, route of administration, rate of excretion, and response sensitivity.

The suitable dosage may be administered as a single dose once in a daily or in divided doses daily at regular time intervals as prescribed by the physician or pharmacist. For example, the daily dosage may be 0.1 to 10,000 mg/kg and preferably 1 to 2,000 mg/kg, based on the active ingredient content. The above dosages are exemplary. The optimal dosage to be administered may be determined by a person skilled in the art and may be adjusted by a person skilled in the art depending on a variety of factors, including the type of disease, the severity of the disease, the content of the active ingredient and other ingredients in the composition, the type of formulation, the age, weight, general health conditions, gender, and dietary of the patient, the time of administration, the route of administration, the release rate of the composition, the duration of treatment, and concomitant medications.

The present disclosure relates to a method of preventing or treating infectious diseases by administering, to a mammal, one or more gut microbes against infectious diseases selected from the group consisting of *Oribacterium* sp. JBO3-101 strain (accession number KACC 81250BP) and *Ruminococcus* sp. JBR5-501 strain (accession number KACC 81249BP) or cultures thereof.

EXAMPLE

Hereinafter the present disclosure will be described in greater detail with reference to examples. However, these examples are intended to describe the present disclosure in more detail, and the scope of the present disclosure is not limited by the examples.

Example 1: Identifying Gut Microbes Resistant Against Infectious Diseases

Figure 2:
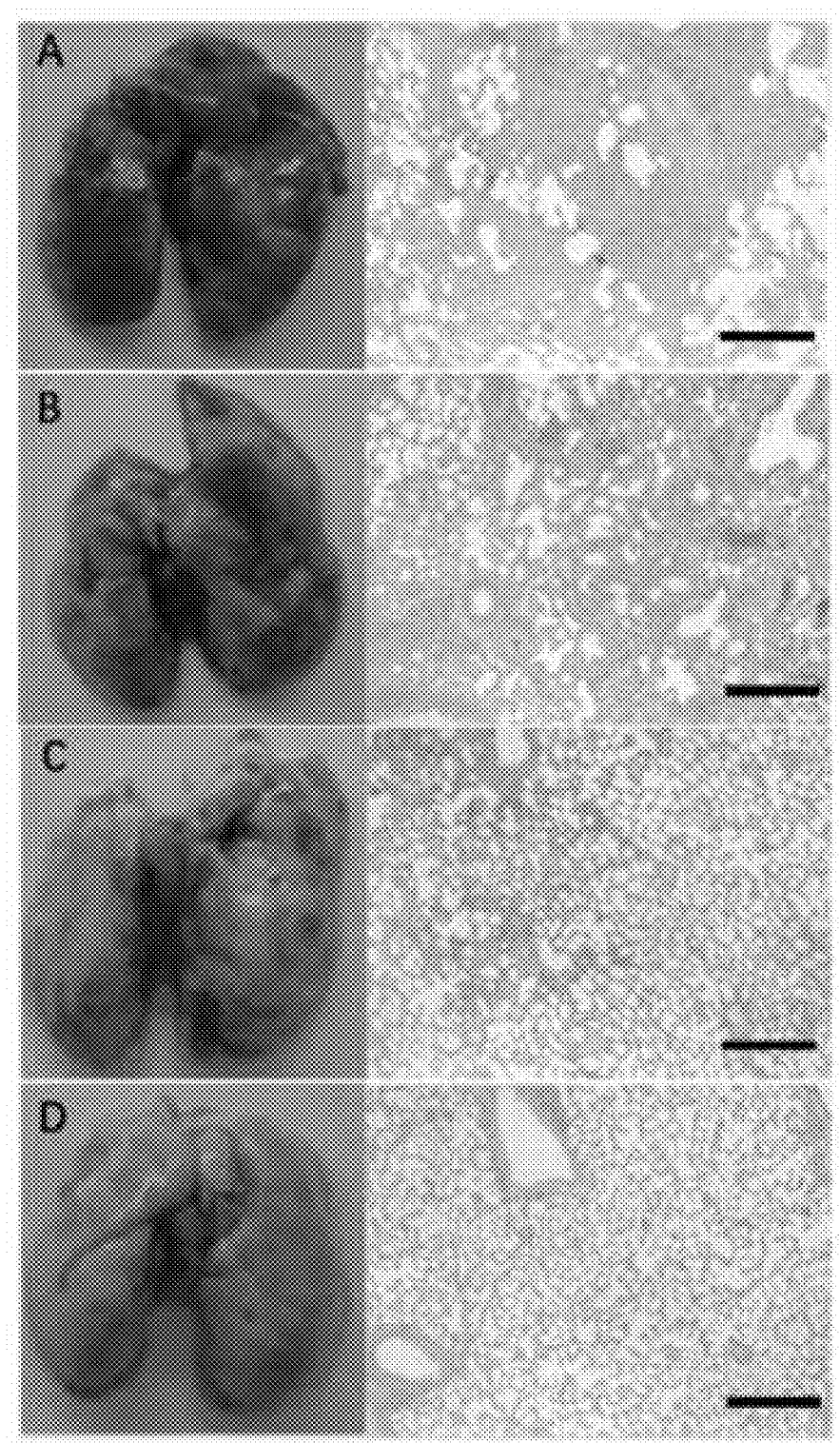
FIG. 2 shows photographs of the lung and H&E-stained photographs of lung tissue of experimental animals classified by degree of infection with SARS-CoV-2 virus after ingestion of an infection-resistant human gut microbe according to Example 1 of the present disclosure (A: control group, B: severely infected group, C: mildly infected group, D: non-infected group).

To identify gut microbes against infectious diseases, the inventors screened the gut microbes of infection-resistant people who had not been infected when exposed to pathogenic microorganisms. For this purpose, Roborovski hamsters SH101 aged 6 weeks or older as experimental animals were given an antibiotic/antimicrobial complex consisting of azithromycin (15 mg/kg), neomycin (25 mg/kg), ciprofloxacin (20 mg/kg), and miconazole (30 mg/kg). Next, feces of infection-resistant people who had never contracted COVID-19 were sampled and prepared in a fresh state as 0.1 g to 0.5 g samples, and the samples were fed to the experimental animals whose gut microbes had been depleted due to the antibiotic/antimicrobial complex. One week later, 50 µl of $10^5$ $TCID_{50}$ of SARS-CoV-2 virus was infected into the noses of the animals with de novo microbiomes. Body temperature was measured daily for the next 7 days (se FIG. 1), and on the eighth day of infection, the lung organs were visually observed through necropsy of the animals in each test group, and lung tissue was stained with H/E to identify pathological changes (see FIG. 2). On the basis of the results, the animals were categorized into severely infected, mildly infected, and non-infected groups according to the degree of fever and lung tissue infection, which are typical symptoms of SARS-CoV-2 infection (see Table 1).

TABLE 1

| Degree of infection | Control | Feces-fed test group |
|---|---|---|
| Severely infected | 6/6 | 6/15 |
| Mildly infected | 0/6 | 5/15 |
| Non-infected | 0/6 | 4/15 |

To perform gut microbe analysis for SARS-CoV-2 virus severely infected, mildly infected, and non-infected groups, all intestinal contents were obtained from the experimental animals of each group, and their 16S rRNA hypervariable regions V3 and V4 were analyzed by 16S metagenomic sequencing. The total number of operational taxonomic units (OTUs) of the gut microbe of each test group was 2,070, and the gut microbe of each test group was allocated to 22 phyla, 153 families, and 278 genera.

Figure 3:
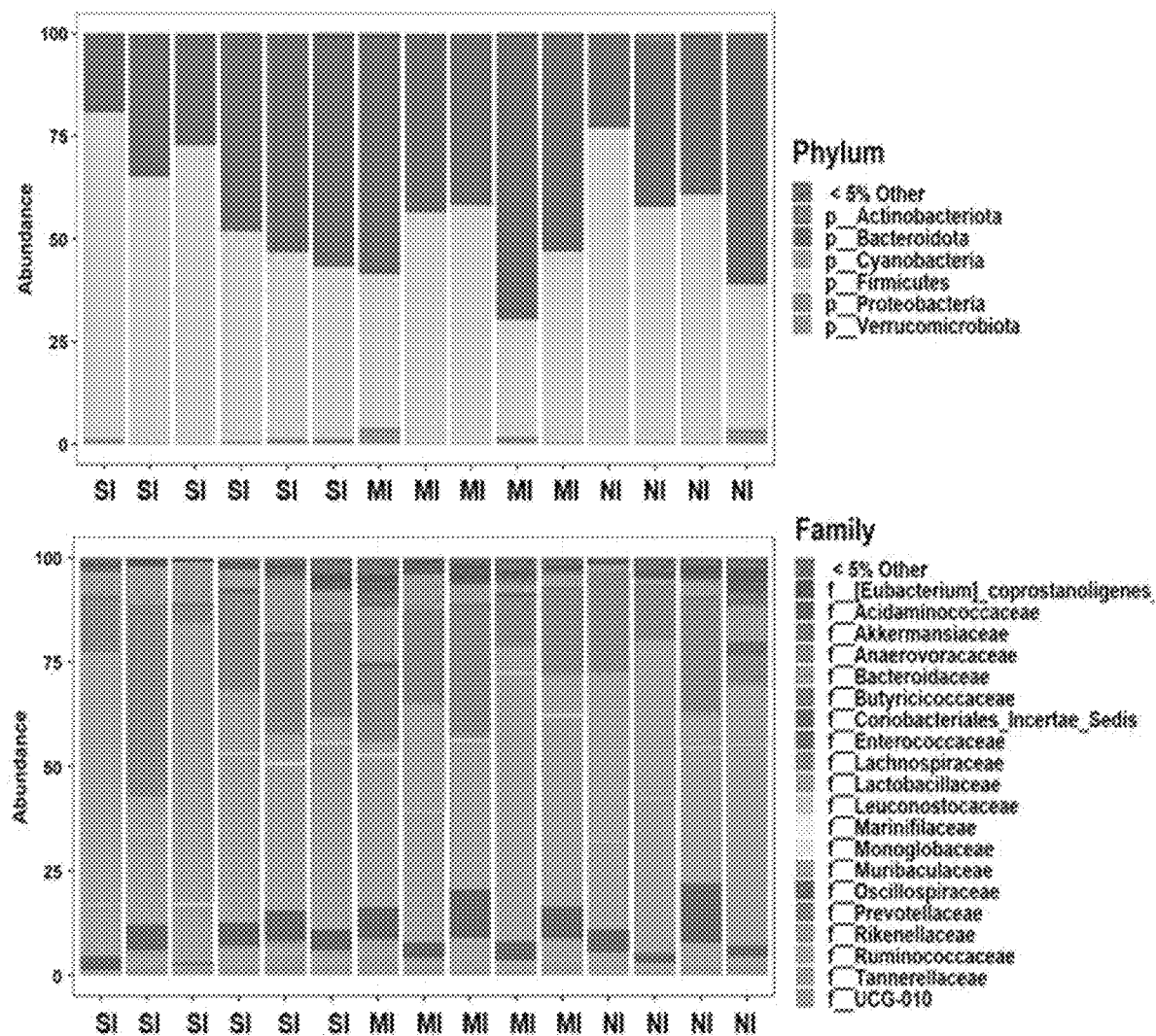
FIG. 3 shows the relative abundance of a gut microbe at the Phylum and Order level of each group of the severely infected (SI), mildly infected (MI), and non-infected (NI) groups in experimental animals infected with SARS-CoV-2 virus after ingestion of the infection-resistant human gut microbe according to Example 1 of the present disclosure.
Figure 4:
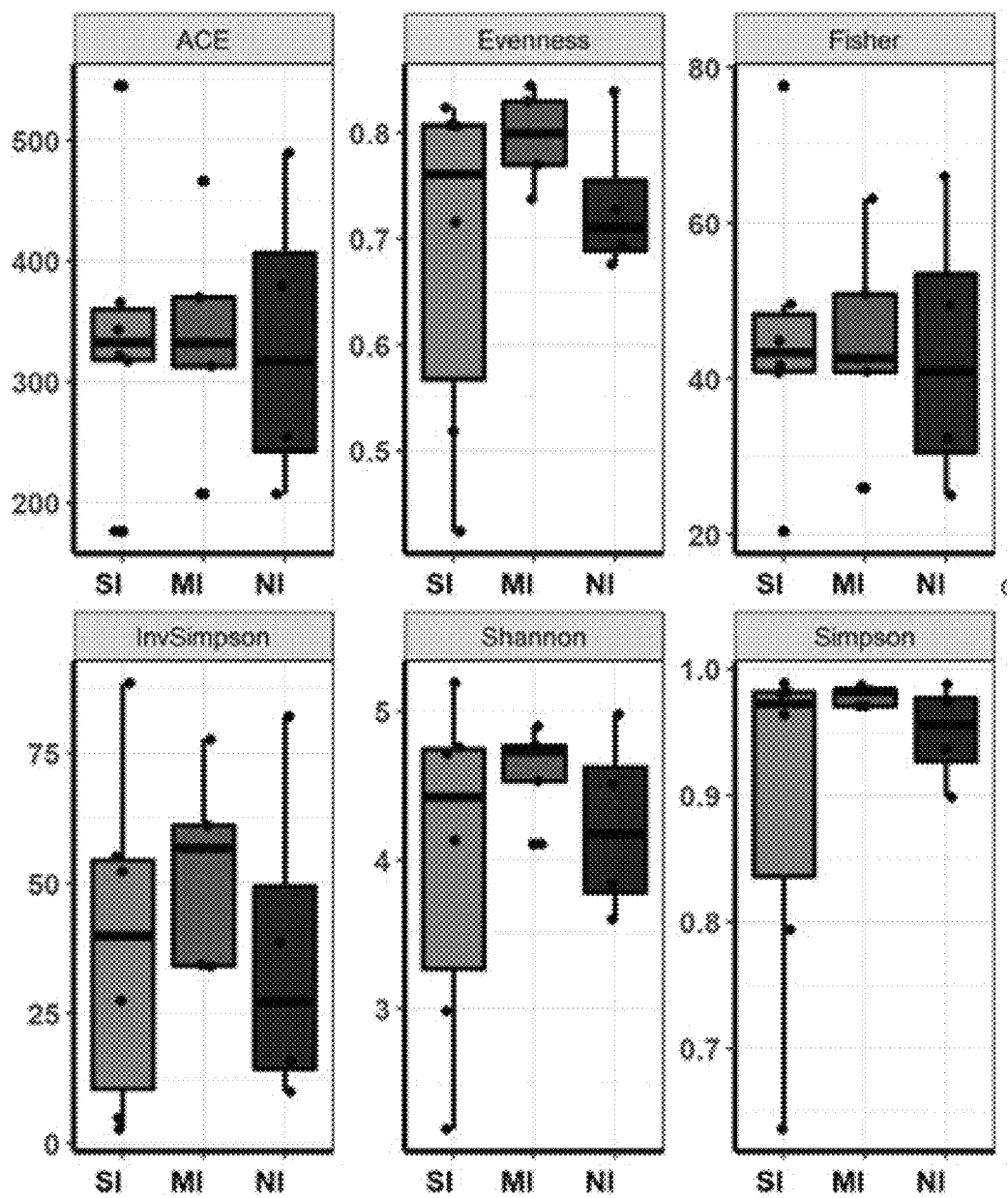
FIG. 4 shows the diversity of the gut microbe of each group of the severely infected (SI), mildly infected (MI), and non-infected (NI) groups in experimental animals infected with SARS-CoV-2 virus after ingestion of the infection-resistant human gut microbe according to Example 1 of the present disclosure, in which the diversity is expressed as alpha diversity.
Figure 5:
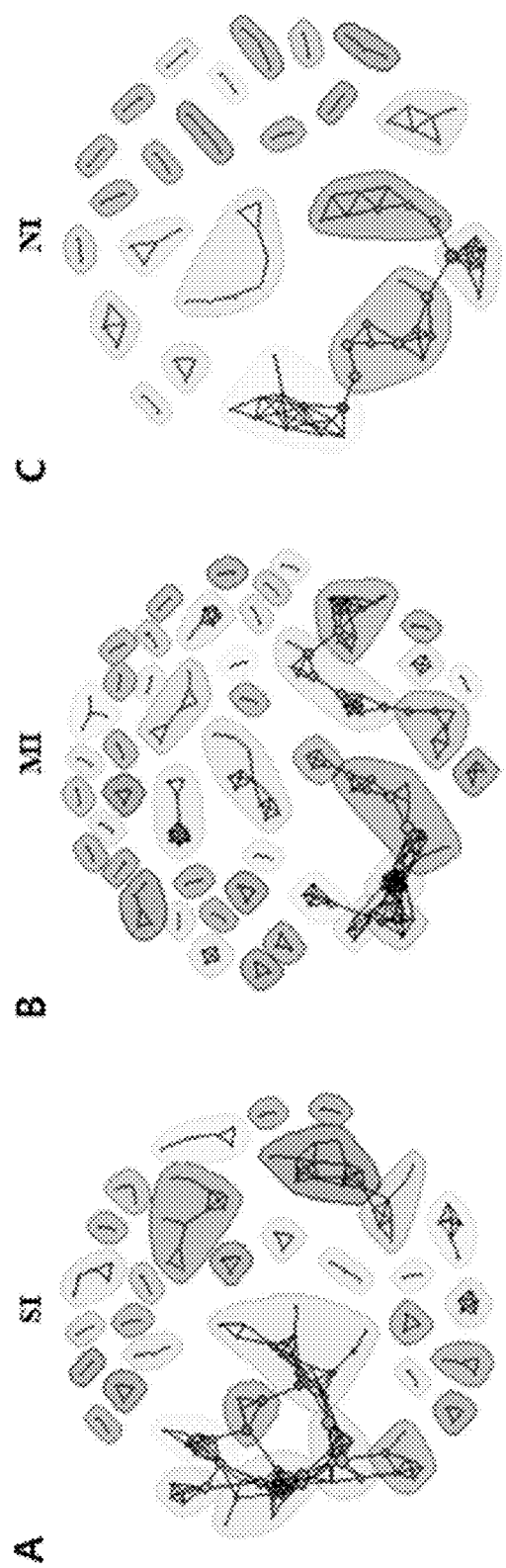
FIG. 5 shows the results of gut microbes co-occurrence network analysis performed using ReBoot algorithm, showing comparison among the severely infected (SI), mildly infected (MI), and non-infected (NI) groups in experimental animals infected with SARS-CoV-2 virus after ingestion of the infection-resistant human gut microbe according to Example 1 of the present disclosure.
Figure 6:
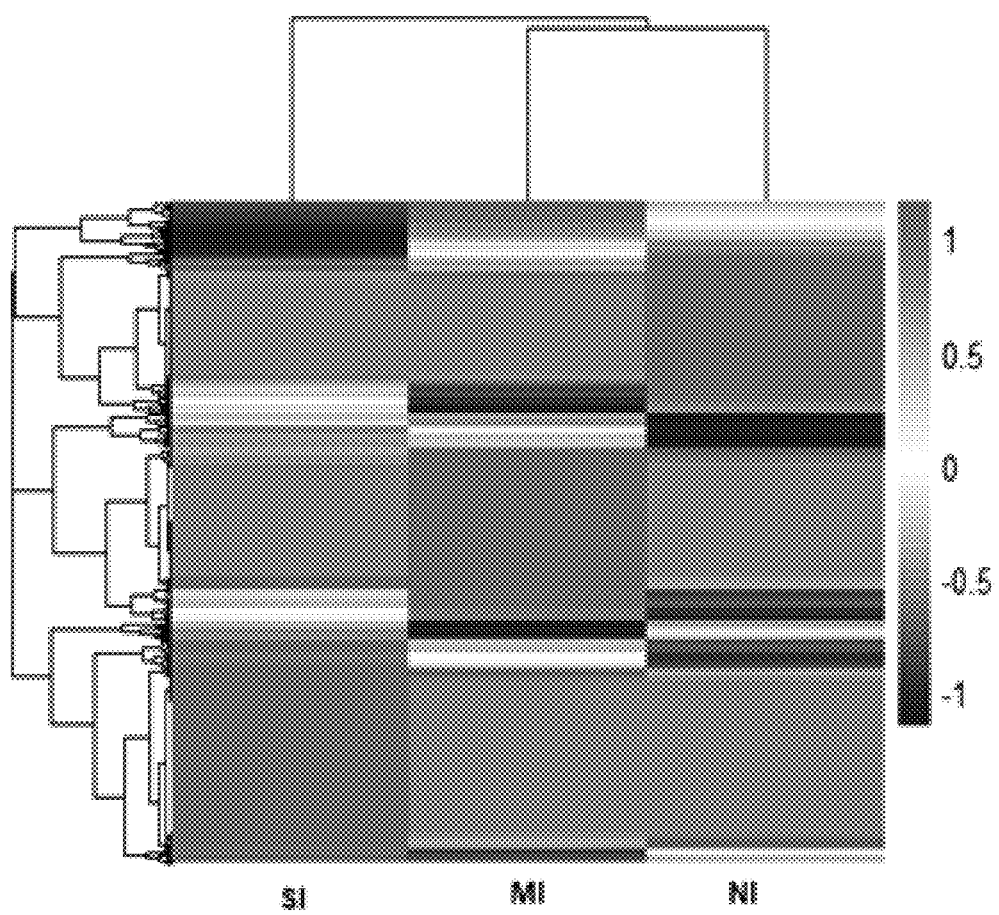
FIG. 6 shows a heatmap result for comparison in gut microbe composition among the severely infected (SI), mildly infected (MI), and non-infected (NI) groups in experimental animals infected with SARS-CoV-2 virus after ingestion of the infection-resistant human gut microbes according to Example 1 of the present disclosure.
Figure 7:
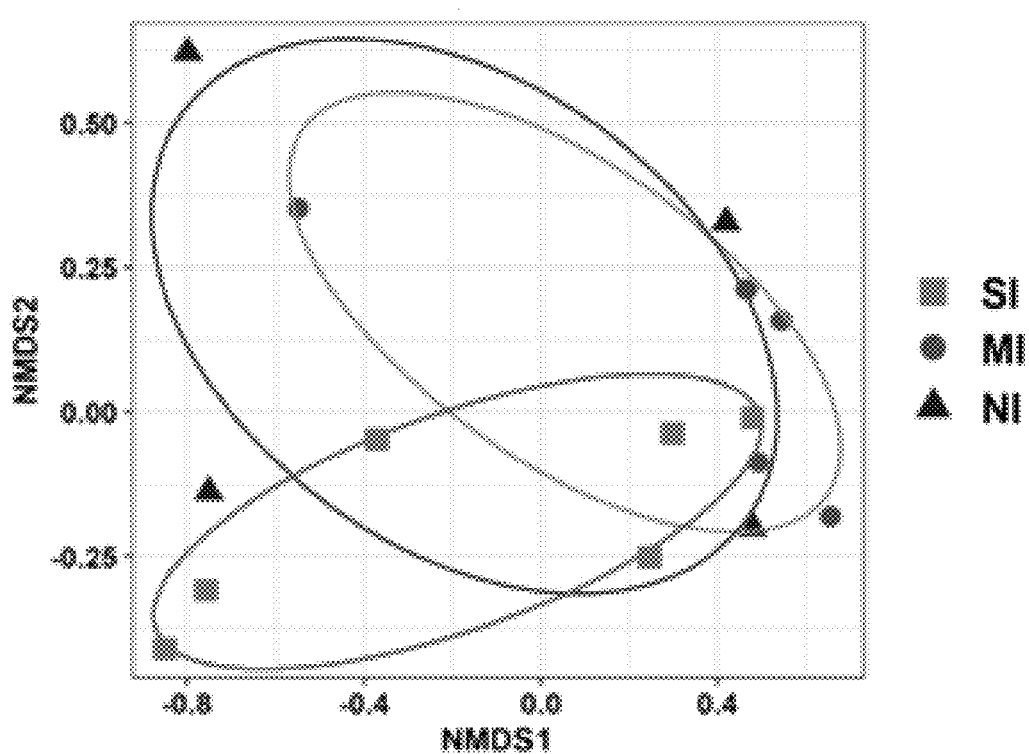
FIG. 7 shows non-metric multidimensional scaling (NMDS) plots showing comparison among the severely infected (SI), mildly infected (MI), and non-infected (NI) groups in experimental animals infected with SARS-CoV-2 virus after ingestion of the infection-resistant human gut microbe according to Example 1 of the present disclosure.
Figure 8:
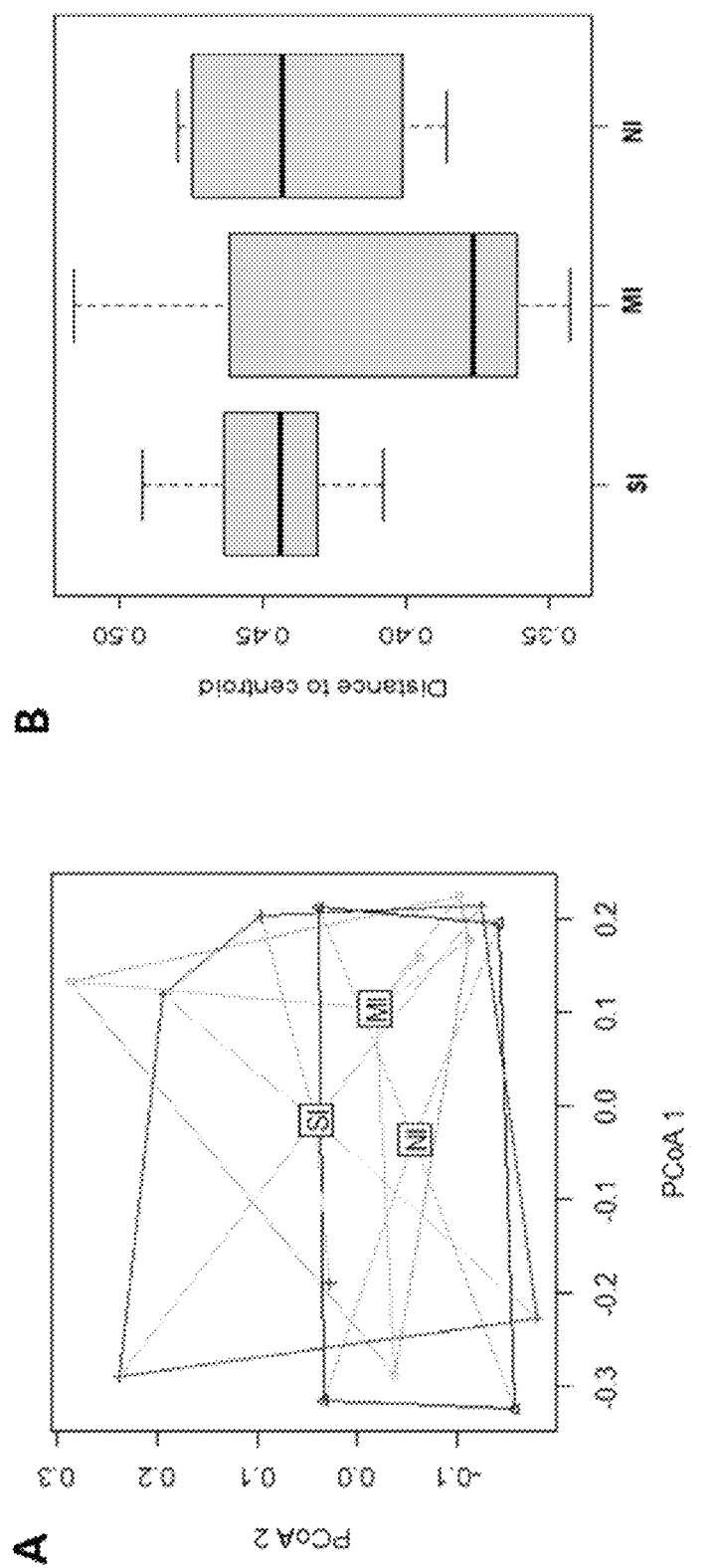
FIG. 8 shows (A) principle component analysis (PCoA) results and (B) distance to the group centroid, for each group of the severely infected (SI), mildly infected (MI), and non-infected (NI) groups in experimental animals infected with SARS-CoV-2 virus after ingestion of the infection-resistant human gut microbe according to Example 1 of the present disclosure.

In experimental animals infected with SARS-CoV-2 virus after ingestion of the infection-resistant human gut microbes, the derived OTUs were used to analyze the gut microbes of the severely infected (SI), mildly infected (MI), and non-infected (NI) groups, and the abundance, alpha-diversity, and co-occurrence network analysis results of each group were compared (FIGS. 3 to 5). The total number of OTUs analyzed was n=974 in the severely infected (SI) group, n=869 in the mildly infected (MI) group, and n=802 in the non-infected (NI) group. The microbe composition of the gut microbes of each group was compared on a heatmap (FIG. 6). The distributions of the groups were compared by non-metric multidimensional scaling (NMDS) plots (FIG. 7). In addition, the distributions in the respective groups were compared by (A) principal component analysis (PCoA) and (B) the distance to the group centroid (FIG. 8).

Figure 9:
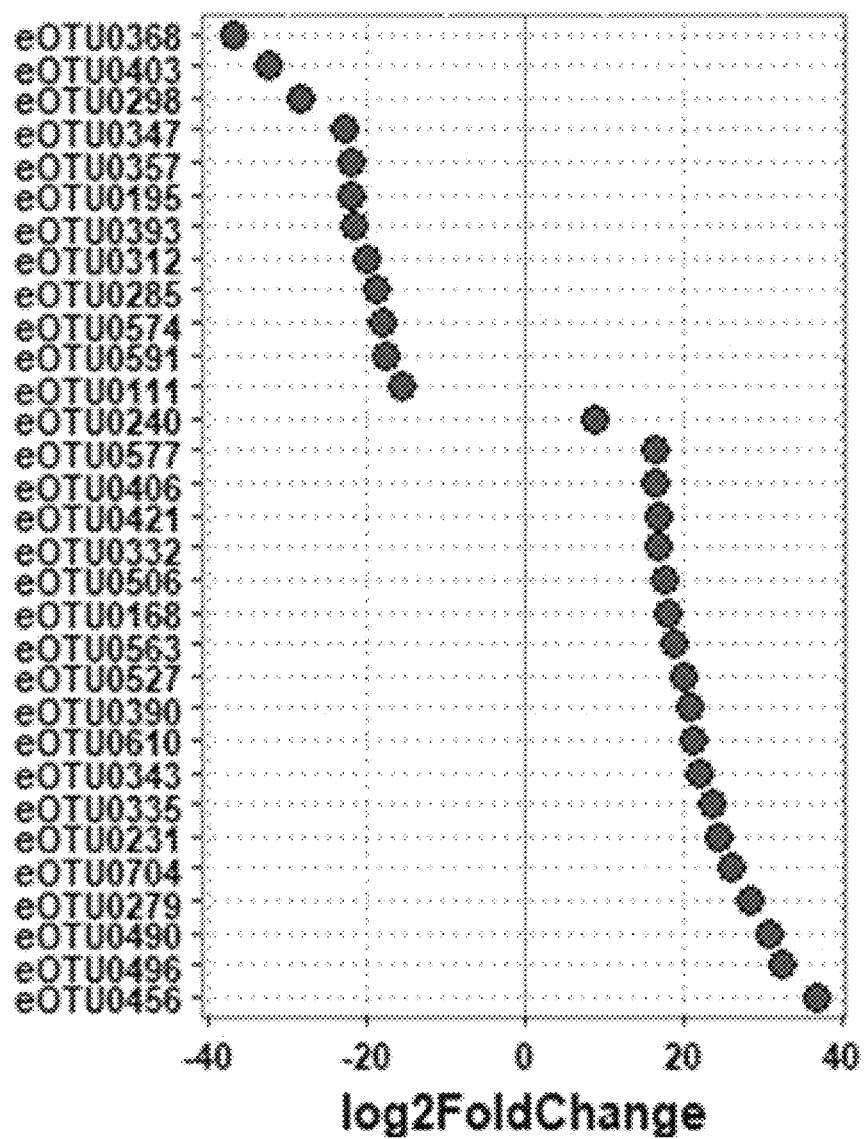
FIG. 9 shows the differential abundance of the gut microbe between the severely infected (SI) group and the non-infected (NI) group in experimental animals infected with SARS-CoV-2 virus after ingestion of the infection-resistant human gut microbe according to Example 1 of the present disclosure, in which the differential abundance of the gut microbe is expressed as log 2 fold change for each OTU, using DESeq2 analysis to analyze the differentially increased microbes between groups at the species level.
Figure 10:
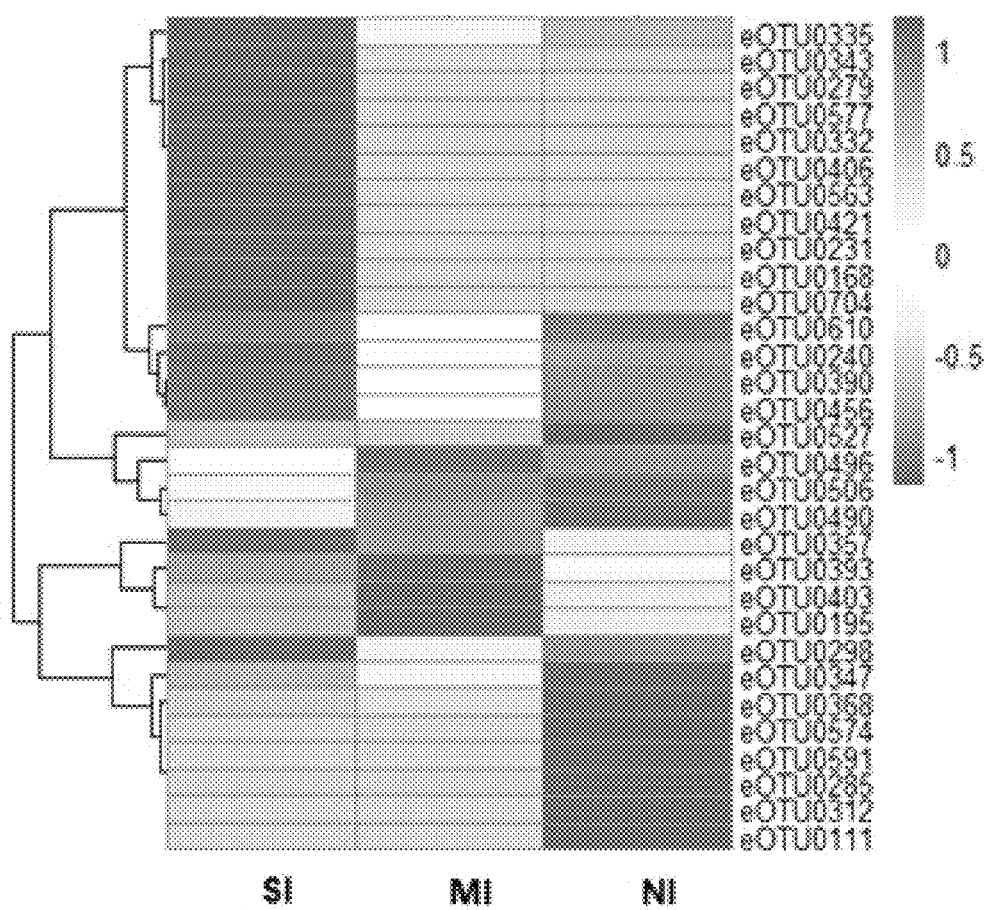
FIG. 10 shows the differential abundance of the gut microbe between the severely infected (SI) group and the non-infected (NI) group in experimental animals infected with SARS-CoV-2 virus after ingestion of the infection-resistant human gut microbe according to Example 1 of the present disclosure, in which the differential abundance of the gut microbe is expressed as log 2 fold change for each OTU, using DESeq2 analysis to analyze the differentially increased microbes between groups at the species level.

FIG. 9 shows the differential abundance of the gut microbes between the severely infected (SI) group and the non-infected (NI) group in experimental animals infected with SARS-CoV-2 virus after ingestion of the infection-resistant human gut microbes according to Example 1 of the present disclosure, in which the differential abundance of the gut microbes is expressed as log 2 change for each OTU through DESeq2 analysis (FIG. 9). Additionally, the clustered heatmap for each OTU was analyzed through DESeq2 analysis (FIG. 10).

As described above, after infection of the experimental animals having the de novo microbiome derived from the infection-resistant person, with SARS-CoV-2 virus according to Example 1 of the present disclosure, the abundance, diversity, composition, and distribution of 2,070 OTUs in the gut microbe were compared among the severely infected (SI) group, the mildly infected (MI) group, and the non-infected (NI) group (FIGS. 3 to 10), and 12 non-infected group-specific OTUs were identified (Table 2).

TABLE 2

| OTU | log2-Fold Change | p value | JB number | Family |
| --- | --- | --- | --- | --- |
| eOTU0368 | −36.79 | 2.26E−20 | JBR5-00501 | Oscillospiraceae |
| eOTU0403 | −32.32 | 5.13E−16 | JBP11-00301 | Porphyromonadaceae |
| eOTU0298 | −28.05 | 1.77E−12 | JBC12-01801 | Clostridiaceae |
| eOTU0347 | −22.6 | 1.35E−08 | JBS14-00101 | Lachnospiraceae |
| eOTU0357 | −21.88 | 3.82E−08 | JBP11-00301 | Porphyromonadaceae |
| eOTU0195 | −21.76 | 4.55E−08 | JBO3-00101 | Lachnospiraceae |
| eOTU0393 | −21.61 | 5.64E−08 | JBO3-00101 | Lachnospiraceae |
| eOTU0312 | −19.82 | 6.58E−07 | JBC12-01801 | Clostridiaceae |
| eOTU0285 | −18.56 | 3.46E−06 | JBP11-00301 | Porphyromonadaceae |
| eOTU0574 | −17.95 | 7.74E−06 | JBP11-00301 | Porphyromonadaceae |
| eOTU0591 | −17.51 | 1.32E−05 | JBC12-01801 | Clostridiaceae |
| eOTU0111 | −15.64 | 0.00013 | JBC1-00101 | Campylobacteraceae |

Figure 11:
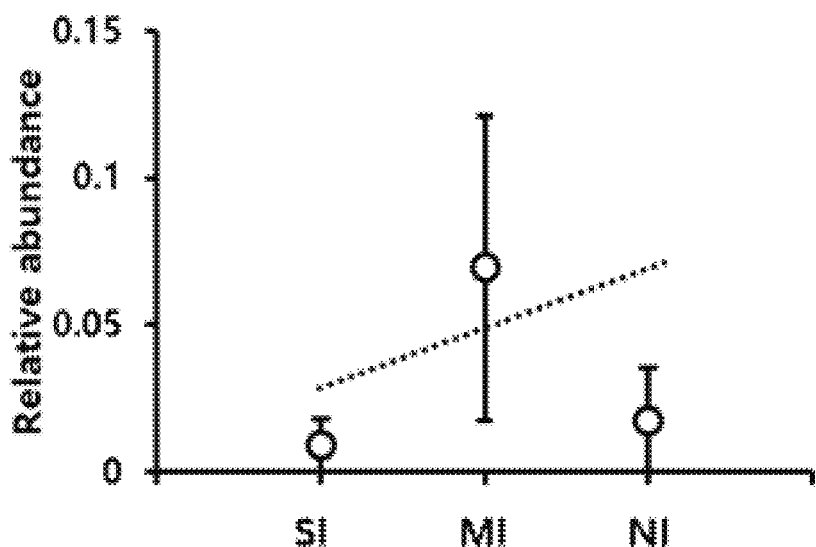
FIG. 11 shows the differential abundance for each group of the severely infected (SI) and non-infected (NI) groups in experimental animals infected with SARS-CoV-2 virus after ingestion of the infection-resistant human gut microbe according to Example 1 of the present disclosure, in which the differential abundance is expressed as the relative abundance of JBO3-101 which is differentially increased.
Figure 12:
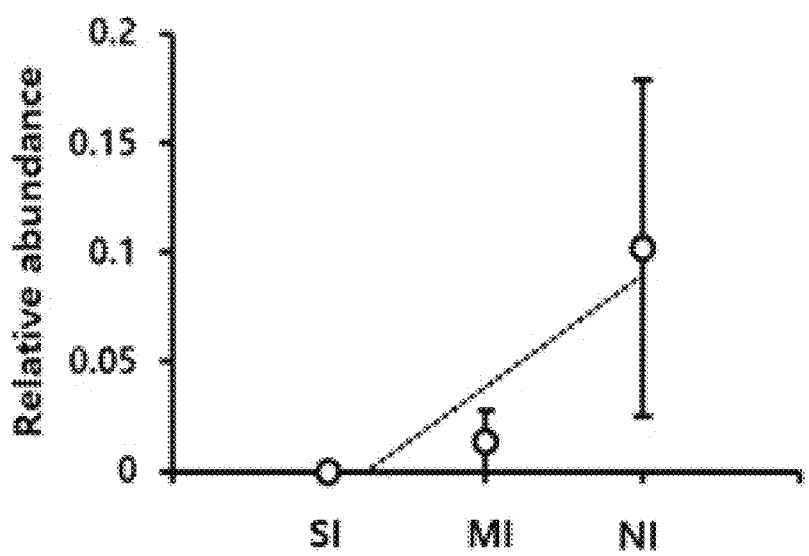
FIG. 12 shows the differential abundance for each group of the severely infected (SI) and non-infected (NI) groups in experimental animals infected with SARS-CoV-2 virus after ingestion of the infection-resistant human gut microbe according to Example 1 of the present disclosure, in which the differential abundance is expressed as the relative abundance of JBR5-501 which is differentially increased.

Among the six microbes corresponding to the 12 non-infected group OTUs, JBO3-101 and JBR5-501 strains are respectively as a novel strain JBO3-101 belonging to *Oribacterium* species and a novel strain JBR5-501 belonging to *Ruminococcus* species and showed non-infected group (NI) specificity. In fact, when the severely infected (SI) group is compared with the non-infected (NI) group, JBO3-101 (FIG. 11) and JBR5-501 (FIG. 12) showed the significantly increased differential abundance in the non-infected (NI) group, proving that JBO3-101 and JBR5-501 were infection-resistant microbes derived from infection-resistant people.

Figure 13:
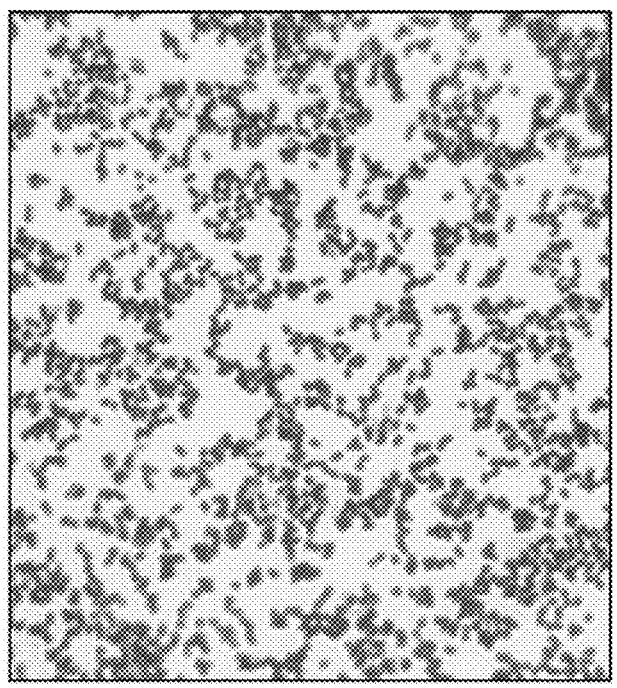
FIG. 13 shows Gram staining photographs of infection-resistant microbes JBO3-101 (A) and JBR5-501 (B) which are found in an infection-resistant human gut microbe according to Example 1 of the present disclosure.
Figure 13:

Referring to Table 2, the morphology of each of the "gut microbes resistant against infectious diseases" JBO3-101 and JBR5-501 identified from the 12 non-infected group-specific OTUs was confirmed by Gram staining (FIG. 13). 16S-rRNA gene sequencing was performed for accurate identification of the strains. Genomic DNA was obtained from each strain and then amplified by PCR using a universal primer set, 27F-AGA GTT TGA TCC TGG CTC AG (SEQ ID NO: 1) and 149R-GGT TAC CTT GTT ACG ACTT (SEQ ID NO: 2), to obtain the base sequences of 16S rRNA (SEQ ID NOs: 3 and 4). The 16S rRNA base sequence of each experimental strain was identified using BLAST search through the NCBI-database. As a result, the "gut microbes resistant against infectious diseases" JBO3-101 and JBR5-501 were identified as new strains JBO3-101 (accession number KACC 81250BP) belonging to *Oribacterium* species and JBR5-501 (accession number KACC 81249BP) belonging to *Ruminococcus* species, respectively, and deposited at the Korean Collection for Type Cultures (KACC) of Biological Resource Center in Korea Research Institute of Bioscience & Biotechnology (KRIBB) on Dec. 20, 2022.

Example 2: COVID-19 Preventive Effect of Gut Microbes Resistant Against Infectious Diseases With the use of JBO3-101 and JBR5-501 strains, which had been identified as infection-resistant microbes, the effectiveness against SARS-CoV-2, the coronavirus that causes COVID-19, the most serious viral infectious disease, was confirmed through animal experiments.

To this end, SARS-CoV-2 HB-01 was obtained from the National Culture Collection for Pathogens (NCCP) of the Korea Illness Control and Anticipation Organization (KDCA). SARS-CoV-2 cultures were prepared by culturing Vero E6 cells in DMEM medium supplemented with 10% FBS, 100 IU/mL penicillin, and 100 μg/mL streptomycin at 37° C., at 5% $CO_2$.

Figure 14:
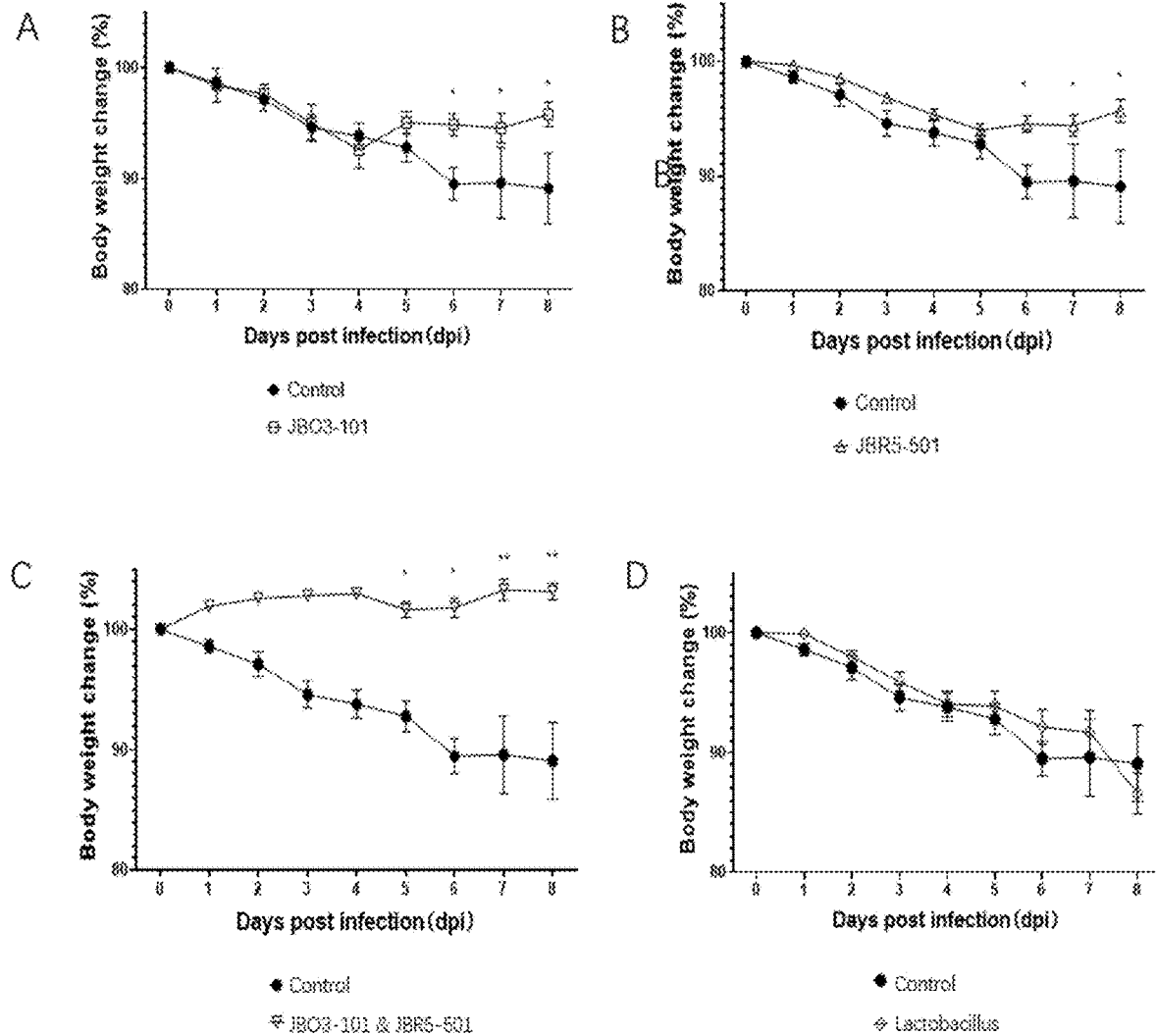
FIG. 14 shows body weights measured daily for 7 days after infection with SARS-CoV-2 virus in experimental animals fed for 1 week with JBO3-101 (A), JBR5-501 (B), or JBO3-101/JBR5-501 (C), which are infection-resistant microbes or experimental animals fed for 1 week with D, *Lactobacillus* sp., which is a control group microbe, according to Example 2 of the present disclosure, compared to the control, which is an infected group.
Figure 15:
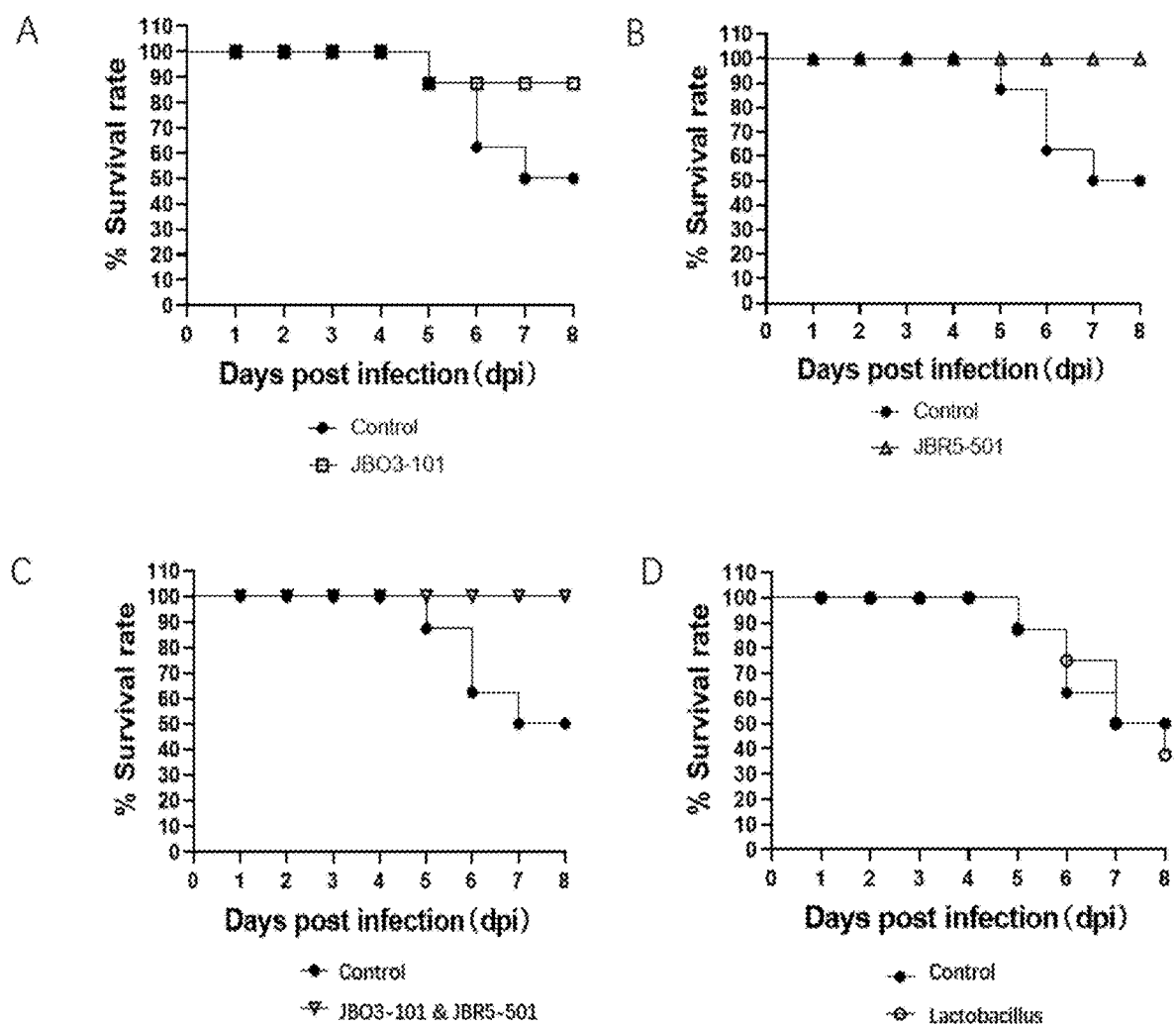
FIG. 15 shows body weights measured daily for 7 days after infection with SARS-CoV-2 virus in experimental animals fed for 1 week with JBO3-101 (A), JBR5-501 (B), or JBO3-101/JBR5-501 (C), which are infection-resistant microbes or experimental animals fed for 1 week with D, *Lactobacillus* sp., which is a control group microbe, according to Example 2 of the present disclosure, compared to the control, which is an infected group.
Figure 16:
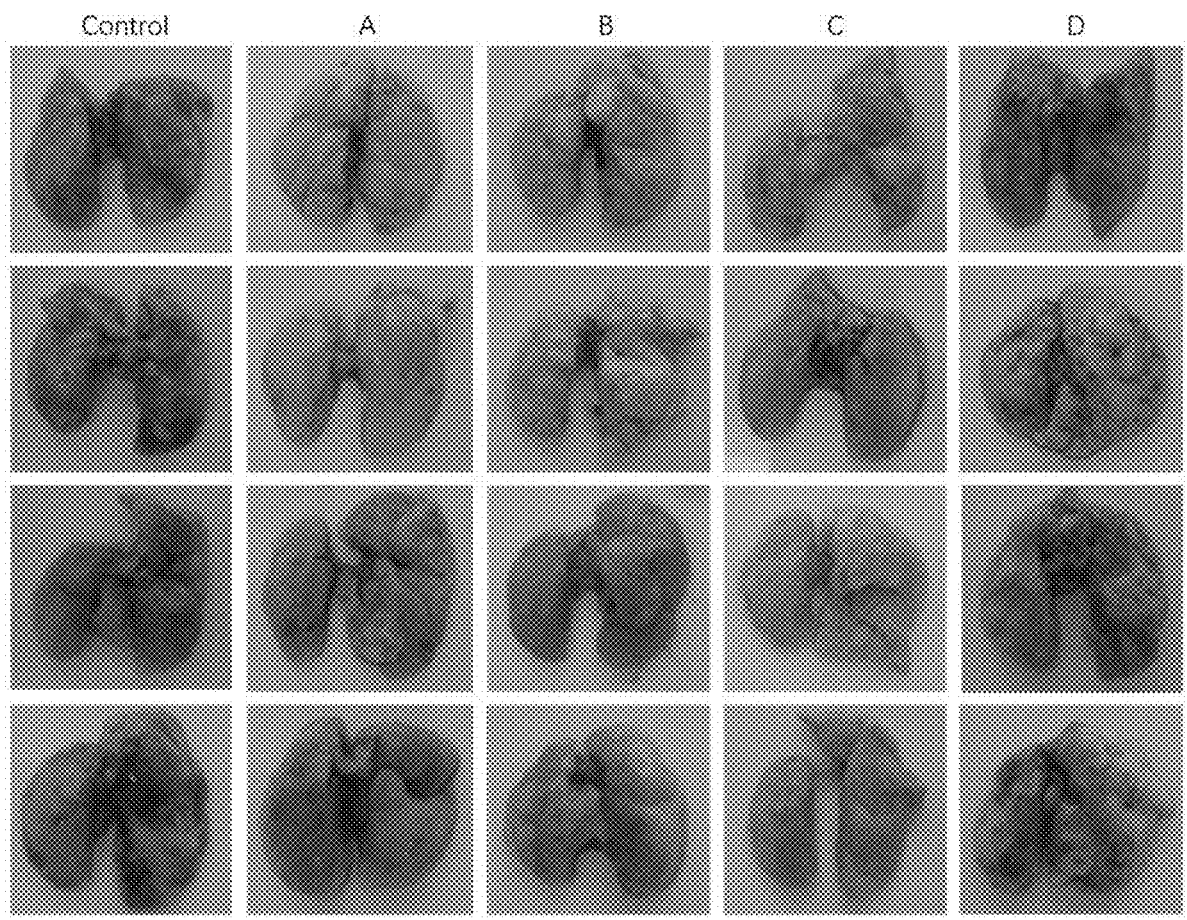
FIG. 16 is a morphologic photograph of lung tissue on day 8 after infection with SARS-CoV-2 virus in experimental animals fed for 1 week with JBO3-101 (A), JBR5-501 (B), or JBO3-101/JBR5-501 (C), which are infection-resistant microbes or experimental animals fed for 1 week with D, *Lactobacillus* sp., which is a control group microbe, according to Example 2 of the present disclosure, compared to the control.
Figure 17:
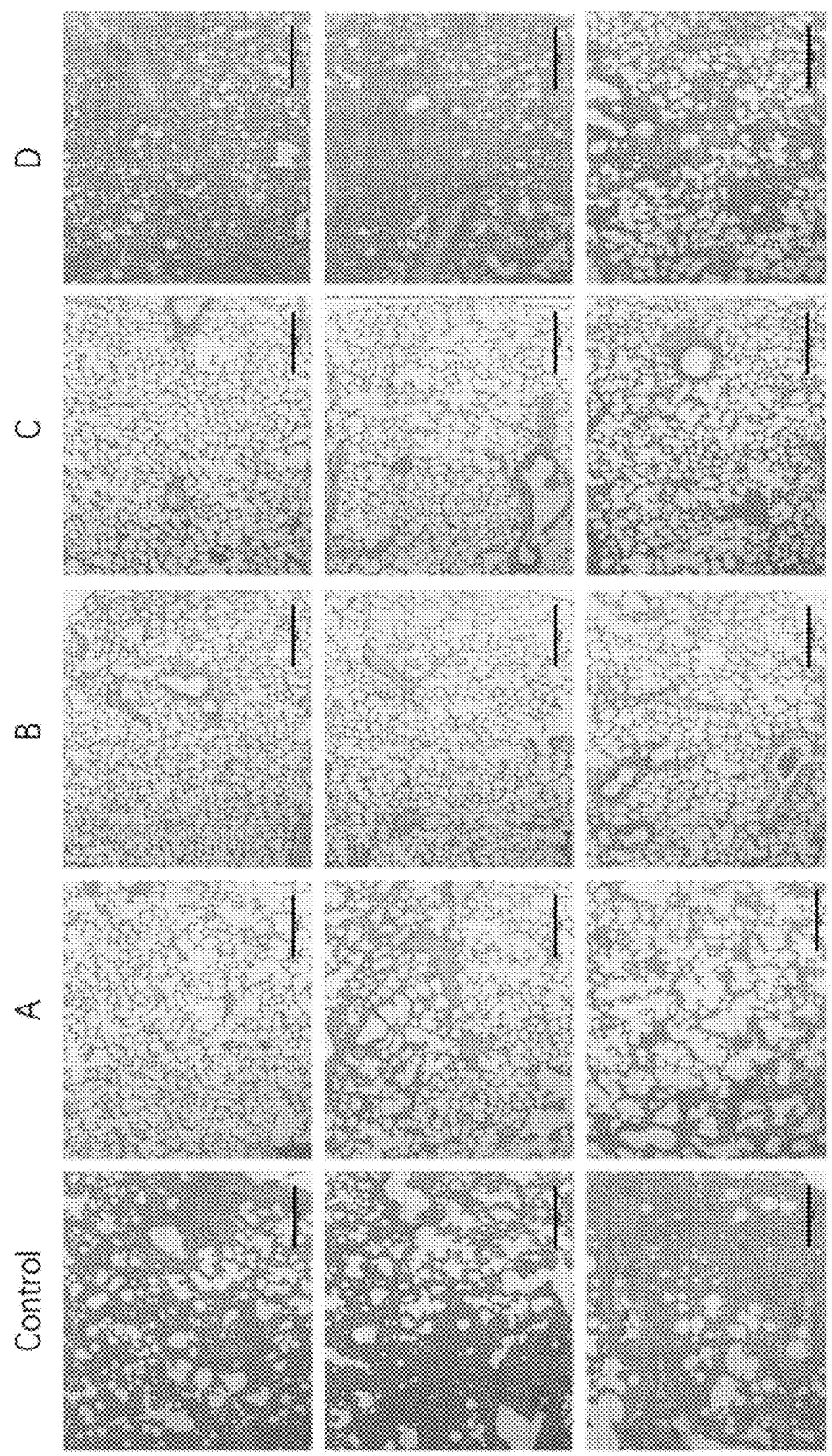
FIG. 17 shows H&E staining photographs of lung tissue sections on day 8 after infection with SARS-CoV-2 virus in experimental animals fed for 1 week with JBO3-101 (A), JBR5-501 (B), or JBO3-101/JBR5-501 (C), which are infection-resistant microbes or experimental animals fed for 1 week with D, *Lactobacillus* sp., which is a control group microbe, according to Example 2 of the present disclosure, compared to the control.
Figure 18:
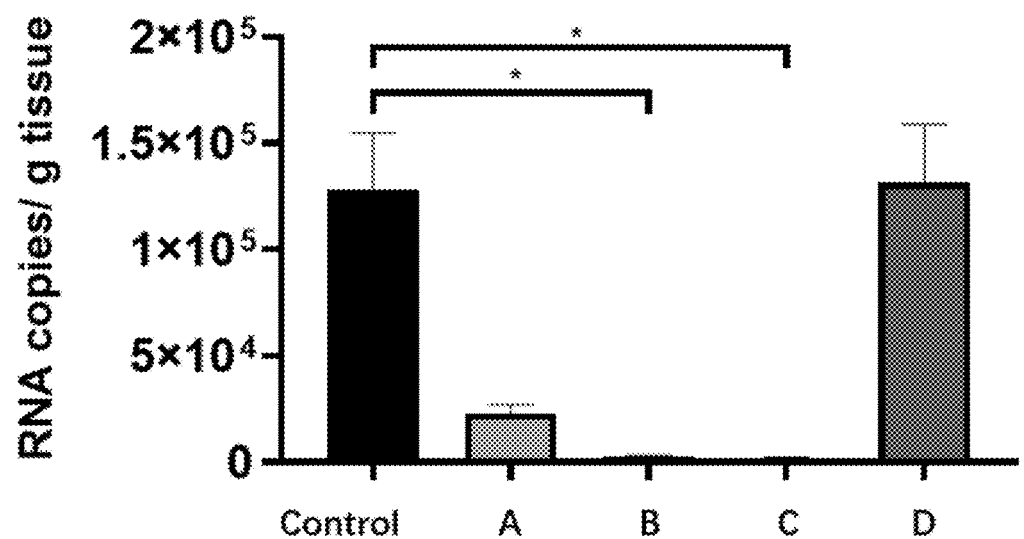
FIG. 18 shows virus RT-PCR results of lung tissue on day 8 after infection with SARS-CoV-2 virus in experimental animals fed for 1 week with JBO3-101 (A), JBR5-501 (B), or JBO3-101/JBR5-501 (C), which are infection-resistant microbes or experimental animals fed for 1 week with D, *Lactobacillus* sp., which is a control group microbe, according to Example 2 of the present disclosure, compared to the control.

Roborovski hamsters (*Phodopus roborovskii*) SH101 (Alpha biochemicals Co.), which are animal models that are highly susceptible to pathogenic microbial infections, were used as experimental animals. The hamsters were raised without restrictions of food (D12450B; Research Dicts Inc.) and drinking water, and the experiments were started after a 1-week acclimatization period at the ABL3 laboratory of Jeonbuk National University. First, an antibiotic mixture of 15 mg/kg of azithromycin, mg/kg of neomycin, 20 mg/kg of ciprofloxacind 30 mg/kg of miconazole was administered to deplete the gut microbes in the hamsters. After 2 days, the hamsters were randomly grouped, and the microbes (gut microbe culture collection) was administered orally to the hamsters of each group at a dose of $1 \times 10^9$ CFU/100 μL PBS/day. After administering the microbes for 1 week, the SH101 hamsters were intranasally infected with SARS-CoV-2 virus at a level of $10^5$ $TCID_{50}$/50 μl. Body weights were recorded daily after the infection (FIG. 14), and death/survival rates were recorded on day 8 of the infection (Table 3 and FIG. 15). All the hamsters were sacrificed, and morphological observations of lung tissue (FIG. 16) and H&E staining of lung sections (FIG. 17) of the hamsters were performed, followed by RT-PCR for virus quantification in the lungs (FIG. 18).

TABLE 3

| Group | Fatality | Survival |
|---|---|---|
| Infection Control | 50% | 50% |
| JBO3-101 | 12.5% | 87.5% |
| JBR5-501 | 0% | 100% |
| JBO3-101 & JBR5-501 | 0% | 100% |
| Lactobacillus sp. | 62.5% | 37.5% |

Referring to the results shown in FIGS. 14 to 18 above, after creating the gut microbes of each experimental animal with the infection-resistant microbes identified from infection-resistant people, the survival rate, weight change, morphological and pathological observations of the lungs, and viral levels upon infection with SARS-CoV-2 virus were quantitatively analyzed. The results revealed that JBO3-101 and JBR5-501 were infection-resistant microbes against SARS-CoV-2 virus infection.

Example 3: Influenza Treatment Effect of Gut Microbes Resistant Against Infectious Diseases With the use of JBO3-101 and JBR5-501 strains, which had been identified as infection-resistant microbes, the effectiveness of treatment against the influenza that causes influenza, which is the most common viral infection disease, was confirmed through animal experiments.

For this purpose, influenza A virus H1N1 (NCCP43021) and strain culturing for virus growth were prepared by culturing MDCK cells in MEM medium containing 10% FBS, 100 IU/mL penicillin, and 100 µg/mL streptomycin at 37° C. at 5% $CO_2$.

Figure 19:
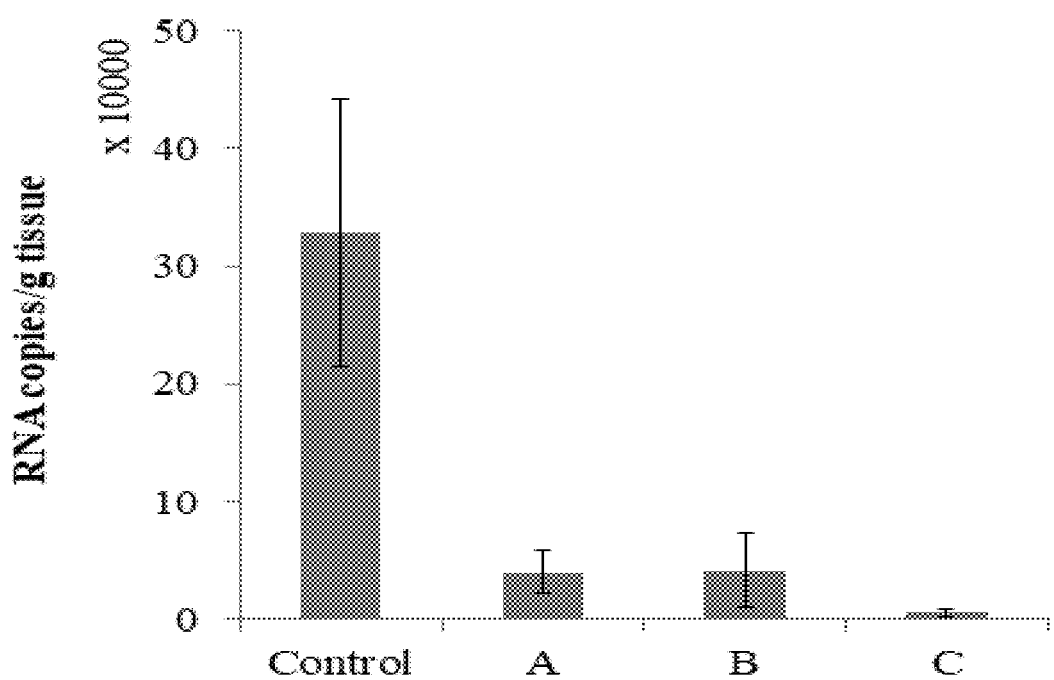
FIG. 19 shows influenza virus RT-PCR results of lung tissue of experimental animals that are first infected with influenza viruses and are then fed for 1 week with JBO3-101 (A), JBR5-501 (B), or JBO3-101/JBR5-501 (C), which are infection-resistant microbes or with D, *Lactobacillus* sp., which is a control group microbe, according to Example 3 of the present disclosure, compared to the control.

Seven-week-old experimental animals, Roborovski hamsters SH101 (Alpha biochemicals Co.), were randomly grouped and intranasally infected with influenza virus at a level of $2 \times 10^3$ PFU/50 µl. For 7 days after the infection, each group (n=5) was orally administered the corresponding microbes JBO3-101 (accession number KACC 81250BP) and JBR5-501 (accession number KACC 81249BP) at a level of $1 \times 10^9$ CFU/100 µL PBS/day. After recording survival rates while monitoring clinical symptoms (Table 4), all the experimental animals were sacrificed, and the lung tissue of each animal was sampled, and RT-PCR was performed for virus quantification (FIG. 19).

TABLE 4

| Group | Survival (%) |
|---|---|
| Infection Control | 60% |
| JBO3-101 | 100% |
| JBR5-501 | 100% |
| JBO3-101 & JBR5-501 | 100% |

After feeding infection-resistant microbes to the experimental animals infected with influenza virus, the survival rate and virus quantification analysis results were obtained. The results confirmed that unlike the control group microbe, JBO3-101 and JBR5-501 were microbes resistant to influenza virus infection.

Figure 20:
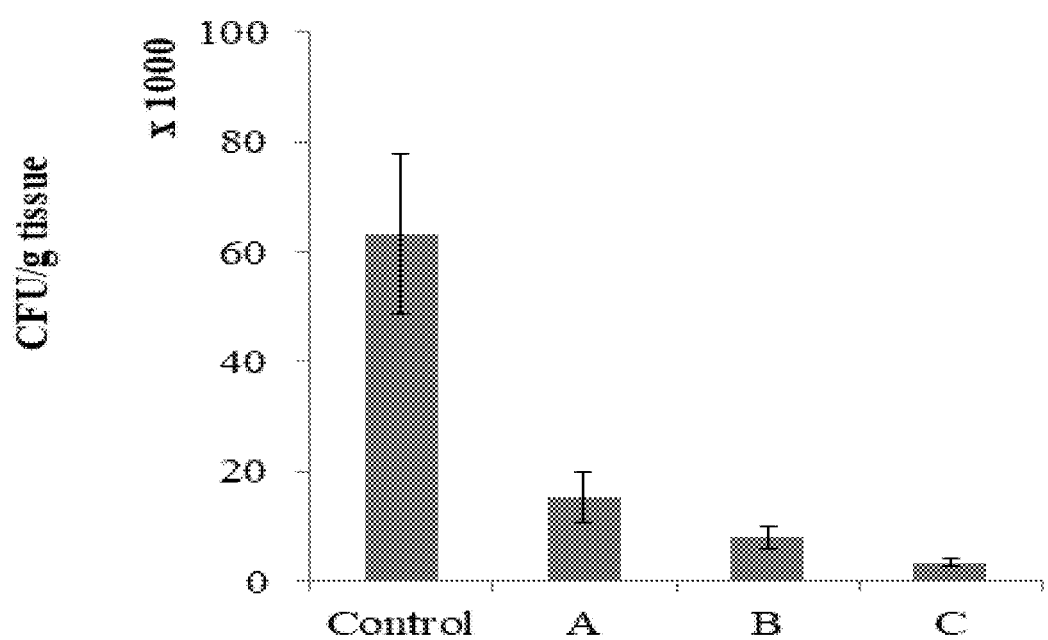
FIG. 20 shows mycobacteria CFU results of lung tissue of experimental animals that are fed for 1 week with JBO3-101 (A), JBR5-501 (B), or JBO3-101/JBR5-501 (C), which are infection-resistant microbes or with D, *Lactobacillus* sp., which is a control group microbe, and are then infected with mycobacteria, according to Example 4 of the present disclosure, compared to the control.

Example 4: Tuberculosis Prevention Effect of Gut Microbes Resistant Against Infectious Diseases With the use of JBR5-501 and JBO3-101 strains, which had been identified as infection-resistant microbes, the effectiveness against *Mycobacterium tuberculosis*, which causes the most serious bacterial infectious diseases, was confirmed through animal experiments. The tuberculosis strain "*Mycobacterium tuberculosis* (NCCP15986)" was prepared by inoculation into 7H10 agar medium containing 50 g albumin, 20 g dextrose, and 8.5 g NaCl per L and then incubation at 37° C. for 10 days. As experimental animals, Roborovski hamsters depleted of the gut microbe were prepared in the same manner as in Example 2. The animals for each group (n=3) were administered the corresponding microbes JBO3-101 (accession number KACC 81250BP) and JBR5-501 (accession number KACC 81249BP) at a level of $1 \times 10^9$ CFU/100 µL PBS/day for 1 week. Next, the experimental animals transplanted with the infection-resistant microbes were intranasally infected with the prepared *M. tuberculosis* culture at a level of $1 \times 10^4$ CFU/50 µl, and survival was recorded by monitoring clinical symptoms for 14 days after infection (Table 5). Afterwards, all the animals were sacrificed, and the CFU of the infectious microbes in the lung tissue was measured (FIG. 20).

TABLE 5

| Group | Survival (%) |
|---|---|
| Infection Control | 33% |
| JBO3-101 | 100% |
| JBR5-501 | 100% |
| JBO3-101 & JBR5-501 | 100% |

After feeding infection-resistant microbes to the experimental animals infected with *Mycobacterium tuberculosis*, the survival rate and quantitative analysis results for *Mycobacterium tuberculosis* were obtained. The results confirmed that JBO3-101 and JBR5-501 were microbes resistant to *Mycobacterium tuberculosis* infection.

[Accession Number]
    Name of Depository: Korean Collection for Type Cultures (KACC), Biological Resource Center in Korea Research Institute of Bioscience & Biotechnology
    Accession Number: KACC81249BP
    Date of Deposit: Dec. 20, 2022
    Name of Depository: Korean Collection for Type Cultures (KACC), Biological Resource Center in Korea Research Institute of Bioscience & Biotechnology
    Accession number: KACC81250BP
    Date of Deposit: Dec. 20, 2022
[Sequence List]
    A sequence list electronic file is attached (C:\KipoEditor\seqFile\1020230004607.xml).

What is claimed is:

1. A gut microbe resistant against infectious diseases, consisting of *Oribacterium* species JBO3-101 strain (accession number KACC 81250BP) and *Ruminococcus* species JBR5-501 strain (accession number KACC 81249BP).

2. The gut microbe of claim 1, wherein the gut microbe has a preventive or therapeutic effect on an infectious disease caused by a pathogenic microorganism.

3. A composition for preventing or treating an infectious disease, wherein the composition comprises, as an active ingredient, a gut microbe resistant against infectious diseases consisting of *Oribacterium* species JBO3-101 strain (accession number KACC 81250BP) and *Ruminococcus* species JBR5-501 strain (accession number KACC 81249BP) or cultures thereof.

4. The composition of claim 3, wherein the infectious disease is a disease caused by infection with a pathogenic virus, a pathogenic bacterium, or a pathogenic fungus.

5. The composition of claim 3, wherein the *Oribacterium* species JBO3-101 strain is at a concentration of $10^3$ to $10^{12}$ CFU/g and the *Ruminococcus* species JBR5-501 strain is at a concentration of $10^3$ to $10^{12}$ CFU/g.

6. The composition of claim 3, wherein the *Oribacterium* species JBO3-101 strain is administered at a dose of $1\times10^9$ CFU/100 μL PBS/day and the *Ruminococcus* species JBR5-501 strain is administered at a dose of $1\times10^9$ CFU/100 μL PBS/day.

* * * * *